(12) United States Patent (10) Patent No.: US 12,642,959 B2

Ahn et al. (45) Date of Patent: Jun. 2, 2026

(54) MICROBLADE FOR ELECTROSTIMULATION

(71) Applicant: AGNES MEDICAL CO., LTD, Seongnam-si (KR)

(72) Inventors: Gunyoung Ahn, Seongnam-si (KR); Hyuck Ki Hong, Yongin-si (KR)

(73) Assignee: AGNES MEDICAL CO., LTD, Seongnam-si (KR)

( * ) Notice: Subject to any disclaimer, the term of this patent is extended or adjusted under 35 U.S.C. 154(b) by 254 days.

(21) Appl. No.: 18/588,023

(22) Filed: Feb. 27, 2024

(65) Prior Publication Data

US 2024/0307676 A1 Sep. 19, 2024

(30) Foreign Application Priority Data

Mar. 17, 2023 (KR) ........................ 10-2023-0035391
Feb. 22, 2024 (KR) ........................ 10-2024-0025477

(51) Int. Cl.
*A61N 1/05* (2006.01)

(52) U.S. Cl.
CPC .................................. *A61N 1/0502* (2013.01)

(58) Field of Classification Search
CPC .................................................... A61N 1/0502
See application file for complete search history.

(56) References Cited

U.S. PATENT DOCUMENTS

2016/0199118 A1* 7/2016 Borgmeier ............. A61B 18/14
606/45
2019/0022371 A1 1/2019 Chang et al.

FOREIGN PATENT DOCUMENTS

KR 10-2013-0012805 A 2/2013

OTHER PUBLICATIONS

Korean Office Action for related KR Application No. 10-2024-0025477 mailed Dec. 18, 2025 from Korean Intellectual Property Office.

* cited by examiner

*Primary Examiner* — Tigist S Demie

(74) *Attorney, Agent, or Firm* — Paratus Law Group, PLLC

(57) ABSTRACT

A microblade for electrostimulation for use in a skin treatment procedure, includes a tip portion formed to be gradually reduced in outer diameter toward a tip and a body portion extending outward from the rear end of the tip portion and having a constant outer diameter. The tip portion includes a first tip edge portion formed by a pair of first tip inclined surfaces, a second tip edge portion formed by a pair of second tip inclined surfaces, and a pair of tip connection surfaces, each interconnecting two adjacent first and second tip inclined surfaces. The body portion includes a first body edge portion formed by a pair of first body inclined surfaces, a second body edge portion formed by a pair of second body inclined surfaces, and a pair of body connection surfaces, each interconnecting two adjacent first and second body inclined surfaces.

13 Claims, 10 Drawing Sheets

MICROBLADE FOR ELECTROSTIMULATION

CROSS-REFERENCE TO RELATED APPLICATIONS

This Application claims priority to Korean Patent Application Nos. 10-2023-0035391 (filed on Mar. 17, 2023) and 10-2024-0025477 (filed on Feb. 22, 2024), which are all hereby incorporated by reference in their entirety.

BACKGROUND OF THE INVENTION

The present invention relates to a microblade for electrostimulation that is used in a skin treatment procedure, and more particularly, to a microblade for electrostimulation capable of improving the efficiency of a skin treatment procedure by forming a high non-radioactive electric field and inducing heat diffusion at a treatment site of the skin into which the microblade is inserted when low power is applied to the microblade.

In general, the skin that covers the human body serves as a primary barrier that protects against the external environment, such as sunlight, cold, and wind. As a person grows older, the skin loses vitality and has wrinkles due to environmental influences.

The skin is largely composed of an epidermal layer having a thickness of about 100 μm, a dermal layer located under the epidermal layer and having a thickness of about 4 mm, and a subcutaneous fat layer located under the dermal layer.

The epidermal layer, which is the outermost layer of the skin, includes various layers, which are divided into a horny layer, a clear layer, a granular layer, a spinous layer, and a basal layer according to the positions and functions thereof, and has protection, defense, and secretion functions.

The dermal layer is located under the epidermal layer and adjacent to the basal layer, and constitutes the majority of the skin. The dermal layer includes a papillary layer, which contains moisture, proteins, saccharides, mucopolysaccharides, minerals, and inorganic salts in the form of gel and in which capillary vessels associated with blood circulation and lymphatic vessels carrying lymph are located, and a reticular layer, which contains collagen that is a collagenous fiber associated with wrinkles of the skin, elastin that is an elastic fiber providing elasticity to the skin, and a ground substance (reservoir of water).

In recent years, much attention has been paid to a skin treatment method of maintaining skin elasticity and minimizing skin aging by directly transmitting electrical energy such as high-frequency current to the dermal layer of the skin through a pin to activate cell tissues.

(Patent Document 1) KR10-2013-0012805 A

Patent Document 1 discloses a skin treatment device using high-frequency energy, which includes a high-frequency generator, a plurality of pins configured to provide high-frequency energy transmitted from the high-frequency generator into the skin, a driving unit configured to provide power to insert the plurality of pins into the skin, and a controller configured to control the driving unit to insert end portions of the plurality of pins to a first target position in the skin and to move the end portions of the pins to a second target position in the state in which the end portions of the pins are inserted into the skin.

In other words, the pin has a pointed distal end and a circular cross-section that is gradually increased in outer diameter toward the proximal end thereof, and electrical energy such as high-frequency current is applied to a procedure site of the skin in the state in which the pointed distal end of the pin is inserted into the epidermal layer and the dermal layer of the skin.

In this case, however, the electrical energy is concentrated on the pointed distal end of the pin, and there is a large difference in electromagnetic field (EMF) between the electrical energy transmitted from the pointed distal end of the pin to the skin and the electrical energy transmitted from the body of the pin having a substantially circular cross-section to the skin. Therefore, the electrical energy is transmitted non-uniformly to a procedure site of the skin into which the pin is inserted, whereby skin treatment effect is deteriorated, and there is a limitation to increasing a ratio of the amount of power applied to the pin to the amount of electrical energy transmitted to the skin.

SUMMARY OF THE INVENTION

The present invention has been made to solve the above problems, and it is an object of the present invention to provide a microblade for electrostimulation capable of improving the efficiency of a skin treatment procedure by forming a high non-radioactive electric field and inducing heat diffusion at a treatment site of the skin into which the microblade is inserted even when low power is applied to the microblade.

The objects of the present invention are not limited to the above-mentioned object, and other objects not mentioned herein will be clearly understood by those skilled in the art from the following description.

BRIEF DESCRIPTION OF THE DRAWINGS

The above and other objects, features, and other advantages of the present invention will be more clearly understood from the following detailed description taken in conjunction with the accompanying drawings, in which.

DETAILED DESCRIPTION OF THE INVENTION

Hereinafter, a microblade for electrostimulation according to an embodiment of the present invention will be described with reference to the accompanying drawings.

Figure 1:
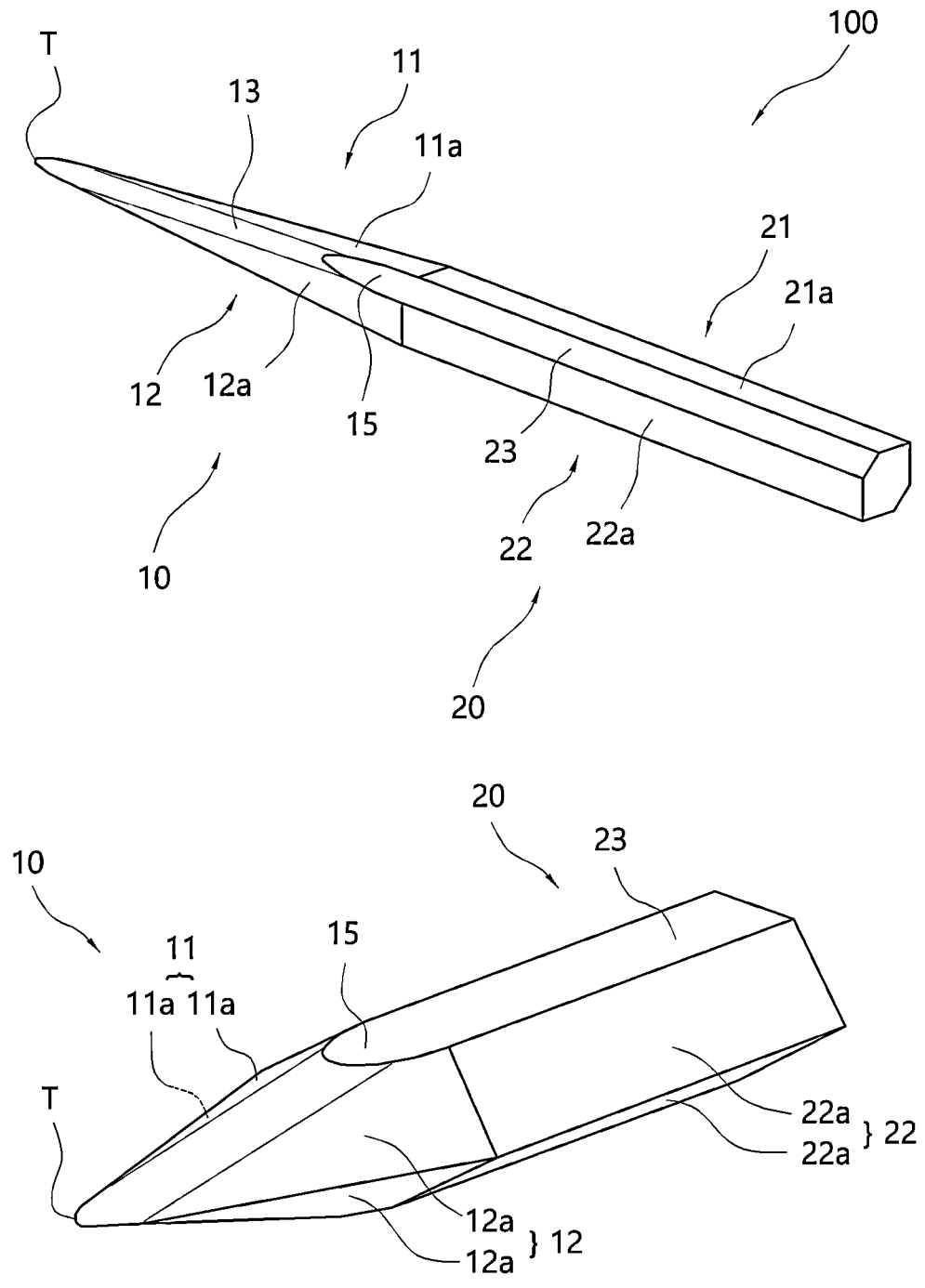
FIG. 1 is a perspective view showing the external appearance of a microblade for electrostimulation according to an embodiment of the present invention.
Figure 2A:
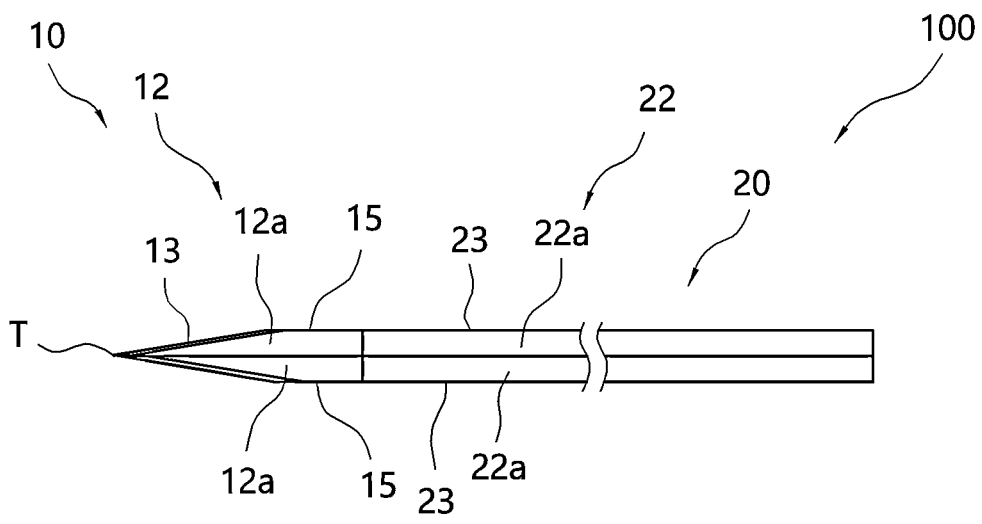
FIG. 2A is a side view of the microblade for electrostimulation according to the embodiment of the present invention.
Figure 2B:
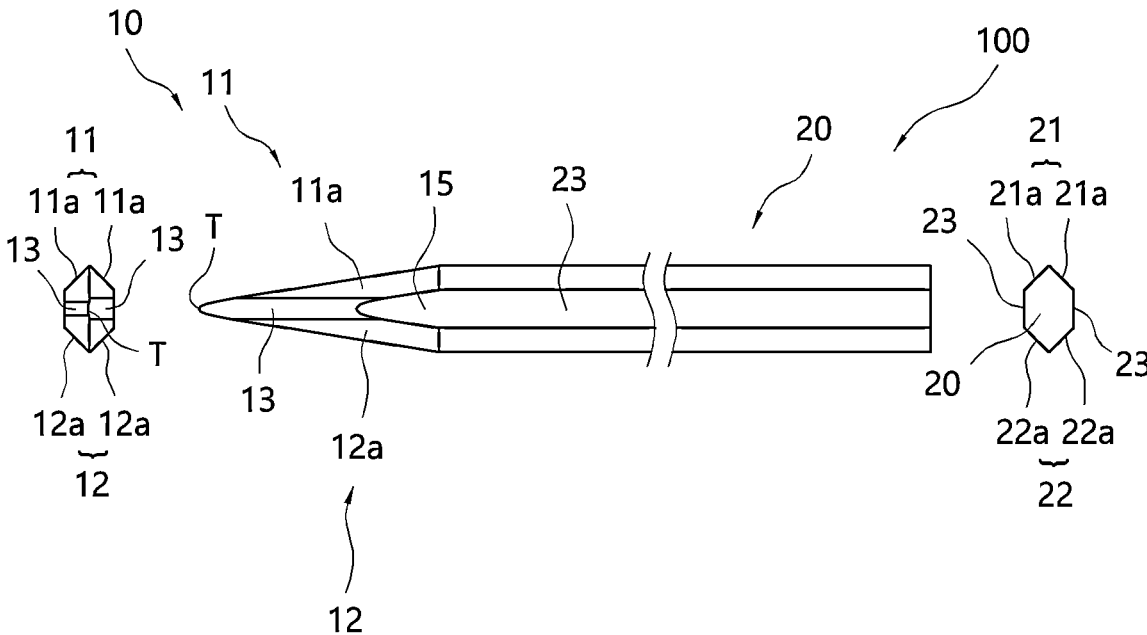
FIG. 2B is a plan view of the microblade for electrostimulation according to the embodiment of the present invention.
Figure 3:
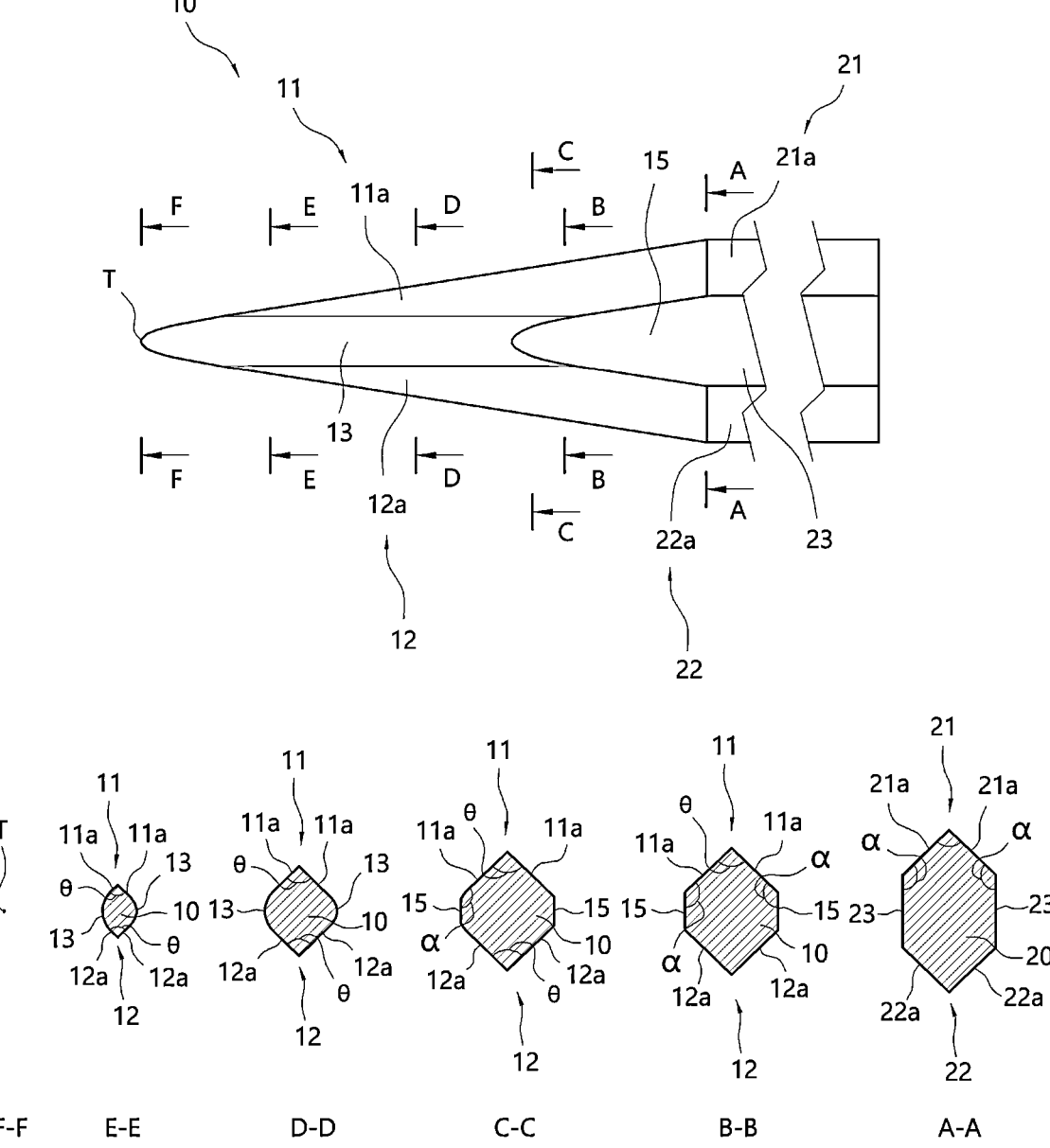
FIG. 3 is a view showing the cross-sectional shapes of a tip portion and a body portion of the microblade for electrostimulation according to the embodiment of the present invention that vary in the longitudinal direction thereof.

FIG. 1 is a perspective view showing the external appearance of a microblade for electrostimulation according to an embodiment of the present invention. FIG. 2A is a side view of the microblade for electrostimulation according to the embodiment of the present invention, and FIG. 2B is a plan view of the microblade for electrostimulation according to the embodiment of the present invention. FIG. 3 is a view showing the cross-sectional shapes of a tip portion and a body portion of the microblade for electrostimulation according to the embodiment of the present invention that vary in the longitudinal direction thereof.

As shown in FIGS. 1, 2A, and 2B, the microblade 100 for electrostimulation according to a preferred embodiment of the invention may include a tip portion 10 and a body present portion 20, which are made of a conductive material, are connected to an external power source, and are inserted to a predetermined depth in the skin to transmit electrical energy, which is an electric field generated when power is applied thereto, to the skin, thereby performing electrostimulation.

Referring to FIGS. 1, 2A, 2B, and 3, the tip portion 10 is a distal end portion that is gradually reduced in outer diameter toward a pointed tip T, which faces a site of the skin that will undergo a procedure.

The tip portion 10 may include a first tip edge portion 11 formed by a pair of first tip inclined surfaces 11a, a second tip edge portion 12 formed by a pair of second tip inclined surfaces 12a, and a pair of tip connection surfaces 13, each of which interconnects one of the pair of first tip inclined surfaces 11a and one of the pair of second tip inclined surfaces 12a adjacent to each other.

In this case, in accordance with the design shape of the tip portion 10 that s gradually reduced in outer diameter toward the pointed tip T, each of the pair of first tip inclined surfaces 11a and the pair of second tip inclined surfaces 12a may be formed in a shape of a planar surface that is gradually reduced in width toward the pointed tip T and is inclined at a predetermined angle toward the pointed tip T and the first and second tip edge portions.

In accordance with the design shape of the tip portion 10 that is gradually reduced in outer diameter toward the pointed tip T, each of the pair of tip connection surfaces 13 may be formed in a shape of a planar surface or a curved surface that is inclined at a predetermined angle toward the pointed tip T while maintaining a constant width and is connected to the pointed tip T.

In this case, each of the pair of tip connection surfaces 13 is preferably formed in a shape of a substantially arc curved surface in order to prevent damage to the skin when the pointed tip T of the tip portion 10 is brought into contact with and inserted into the skin.

Although each of the pair of tip connection surfaces 13 is illustrated and described as being formed in a shape of an arc curved surface, the invention is not limited thereto. Each of the pair of tip connection surfaces 13 may be formed in a shape of a planar surface in order to emit electrical energy, which is an electric field transmitted to the skin through the tip connection surfaces 13, in a direction perpendicular thereto.

The tip portion 10 may include a pair of extension surfaces 15 extending a predetermined length from a pair of body connection surfaces 23 in a boundary area between the tip portion 10 and the body portion 20 so as to be connected to the pair of tip connection surfaces 13 inclined at a predetermined angle. In addition, the thickness of the tip portion 10 decreases toward the pointed end T, and finally, the shape of the pointed end T may have a convex curved shape.

Here, each of the pair of extension surfaces 15 is preferably formed in a shape of a planar surface in order to emit electrical energy, which is an electric field transmitted to the skin when power is applied, in a direction perpendicular thereto together with the pair of body connection surfaces 23 formed in a shape of a planar surface.

An angle θ between the pair of first tip inclined surfaces 11a forming the first tip edge portion 11 and an angle θ between the pair of second tip inclined surfaces 12a forming the second tip edge portion 12 are preferably acute angles smaller than approximately 90° so that the tip portion is easily inserted into the skin by external force.

An angle α between each of the pair of first tip inclined surfaces 11a and an adjacent one of the pair of tip connection surfaces 13 and an angle α between each of the pair of second tip inclined surfaces 12a and an adjacent one of the pair of tip connection surfaces 13 are preferably obtuse angles larger than approximately 90°.

In addition, a vertical distance between the vertex of the first tip edge portion 11 at which the pair of first tip inclined surfaces 11a meet each other and the vertex of the second tip edge portion 12 at which the pair of second tip inclined surfaces 12a meet each other is preferably longer than a horizontal distance between the pair of tip connection surfaces 13 facing each other.

In this case, the vertical distance and the horizontal distance are shortened at the same rate in accordance with the shape design of the tip portion 10 that is gradually reduced in outer diameter toward the pointed tip T.

Accordingly, compared to the conventional conical or cylindrical pin having a substantially circular cross-section, the tip portion 10, which includes the pair of first tip inclined surfaces 11a, the pair of second tip inclined surfaces 12a, and the pair of tip connection surfaces 13, has a polygonal (e.g., substantially hexagonal) cross-section, and is provided on the outer periphery thereof with a plurality of field emission surfaces that emit electrical energy, which is an electric field emitted to the skin when power is applied, in a direction perpendicular thereto.

Due to the structural features as described above, the microblade according to the embodiment of the present invention has a polyhedral shape with angled surfaces as a whole, and may have a polygonal shape in a longitudinal section in a specific area. In addition, while the wound formed on the skin by the penetration of conventional conical or cylindrical pins has a shape of a dot, the wound formed by the microblade according to the embodiment of the present invention may be formed in a straight shape.

Figure 4A:
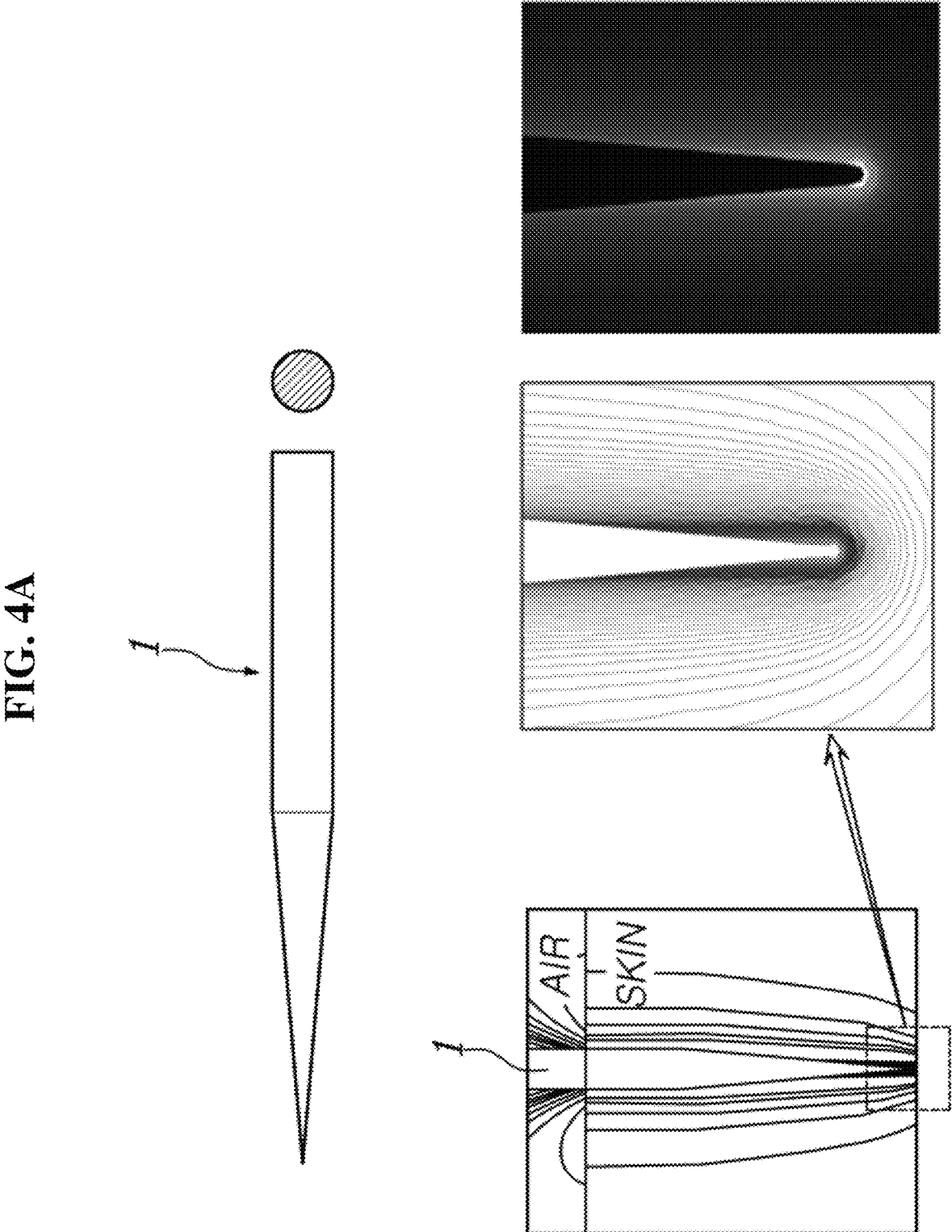
FIG. 4A shows the distribution of an electric field emitted from the conventional conical or cylindrical pin.
Figure 4B:
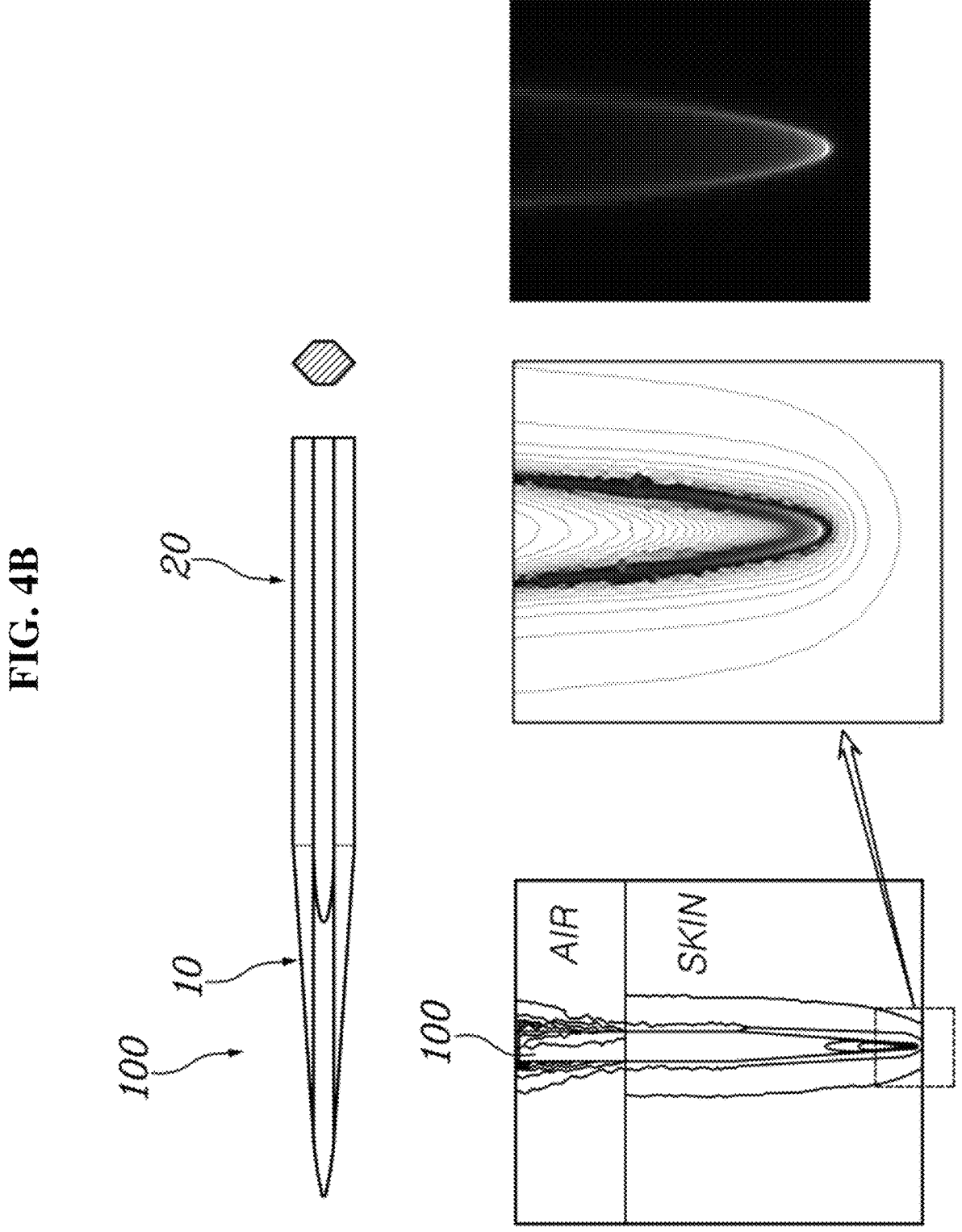
FIG. 4B shows the distribution of an electric field emitted from the microblade for electrostimulation according to the embodiment of the present invention.
Figure 5A:
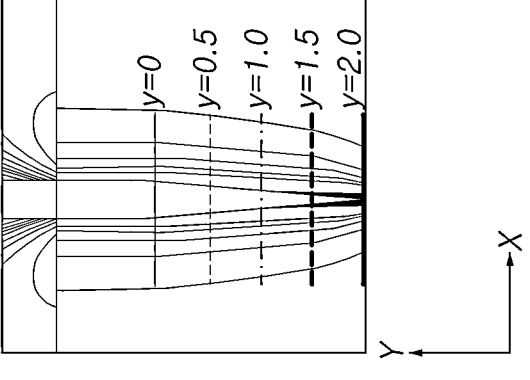
FIG. 5A is a graph showing the electric field intensity at each position in the longitudinal direction of the conventional conical or cylindrical pin.
Figure 5A:
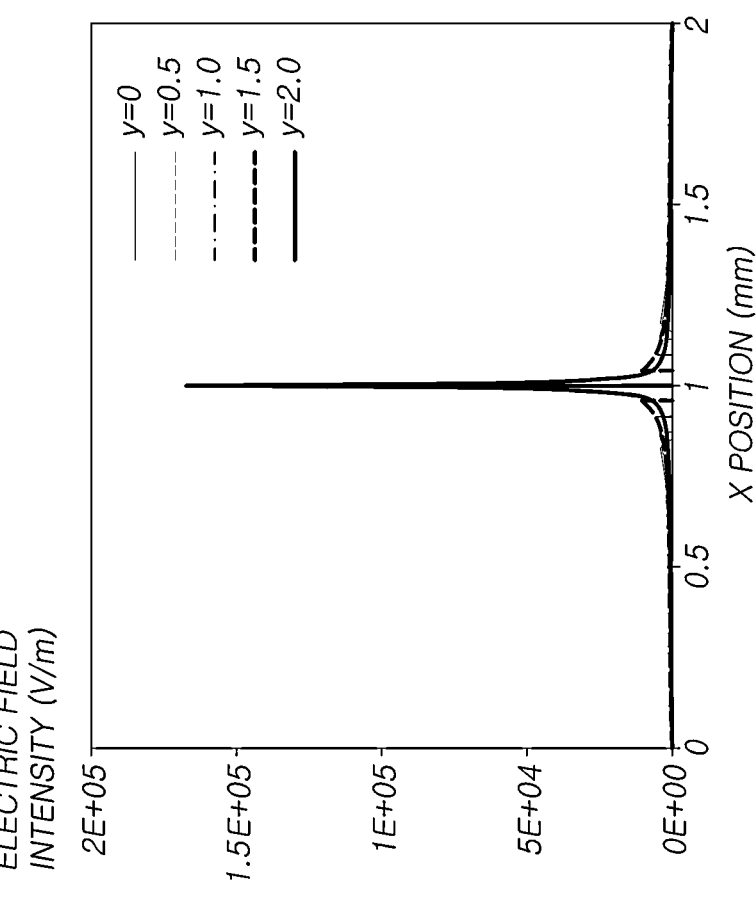
Figure 5B:
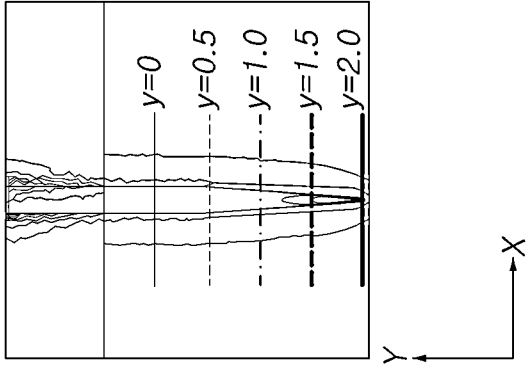
FIG. 5B is a graph showing the electric field intensity at each position in the longitudinal direction of the microblade for electrostimulation according to the embodiment of the present invention.
Figure 5B:
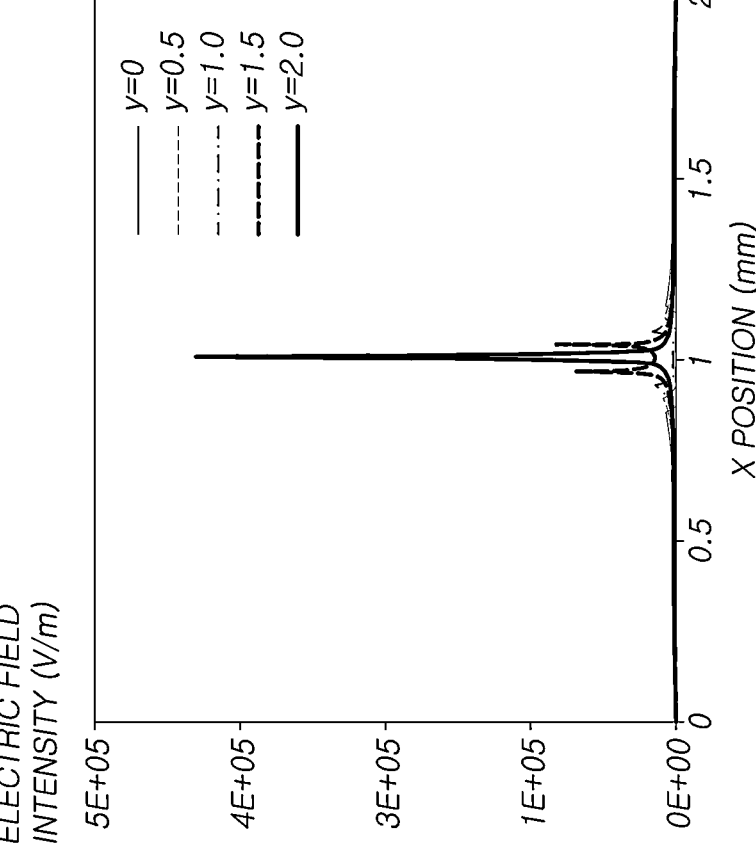
Figure 6A:
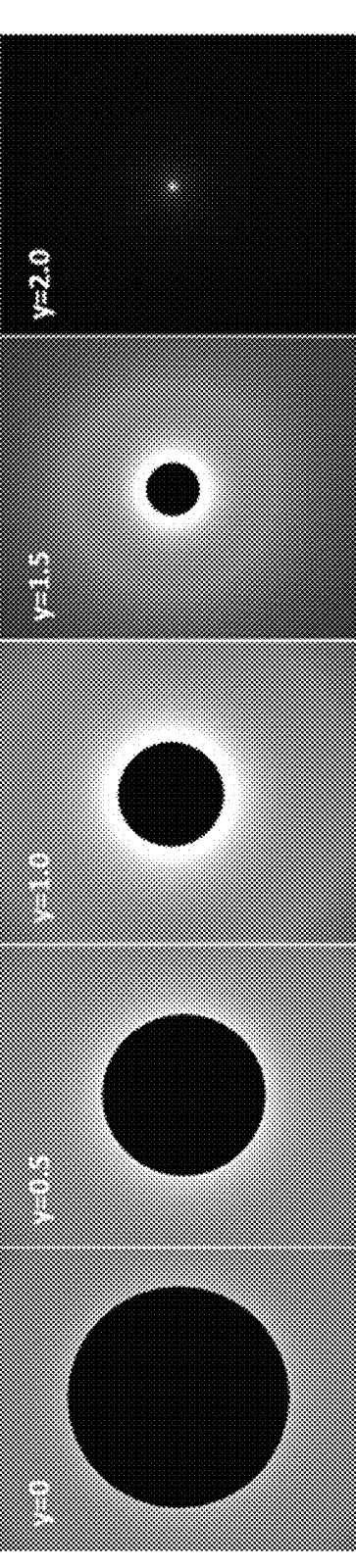
FIG. 6A is a schematic cross-sectional diagram showing the electric field generation state in the longitudinal direction of the conventional conical or cylindrical pin.
Figure 6B:
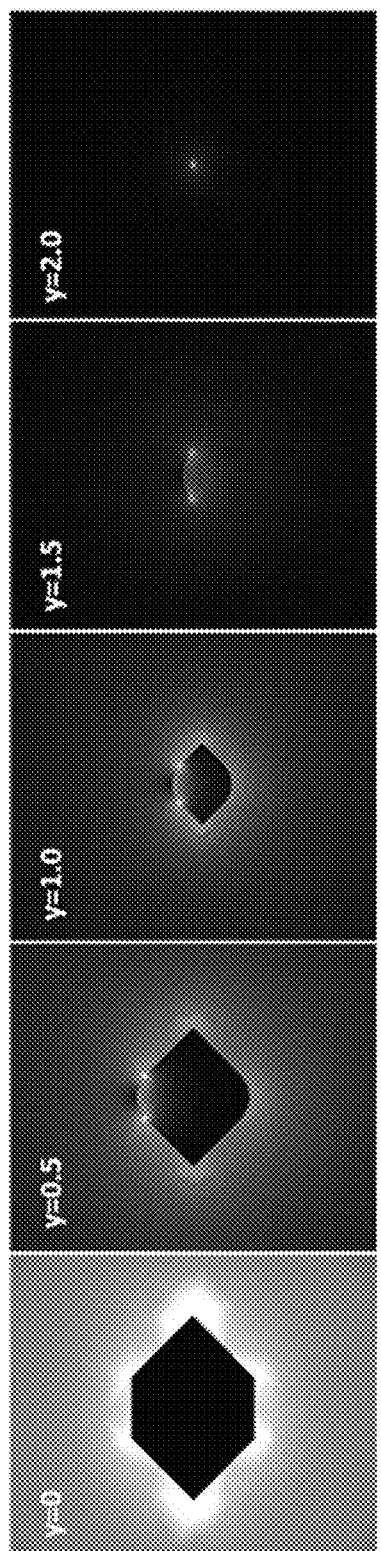
FIG. 6B is a schematic cross-sectional diagram showing the electric field generation state in the longitudinal direction of the microblade for electrostimulation according to the embodiment of the present invention.
Figure 7A:
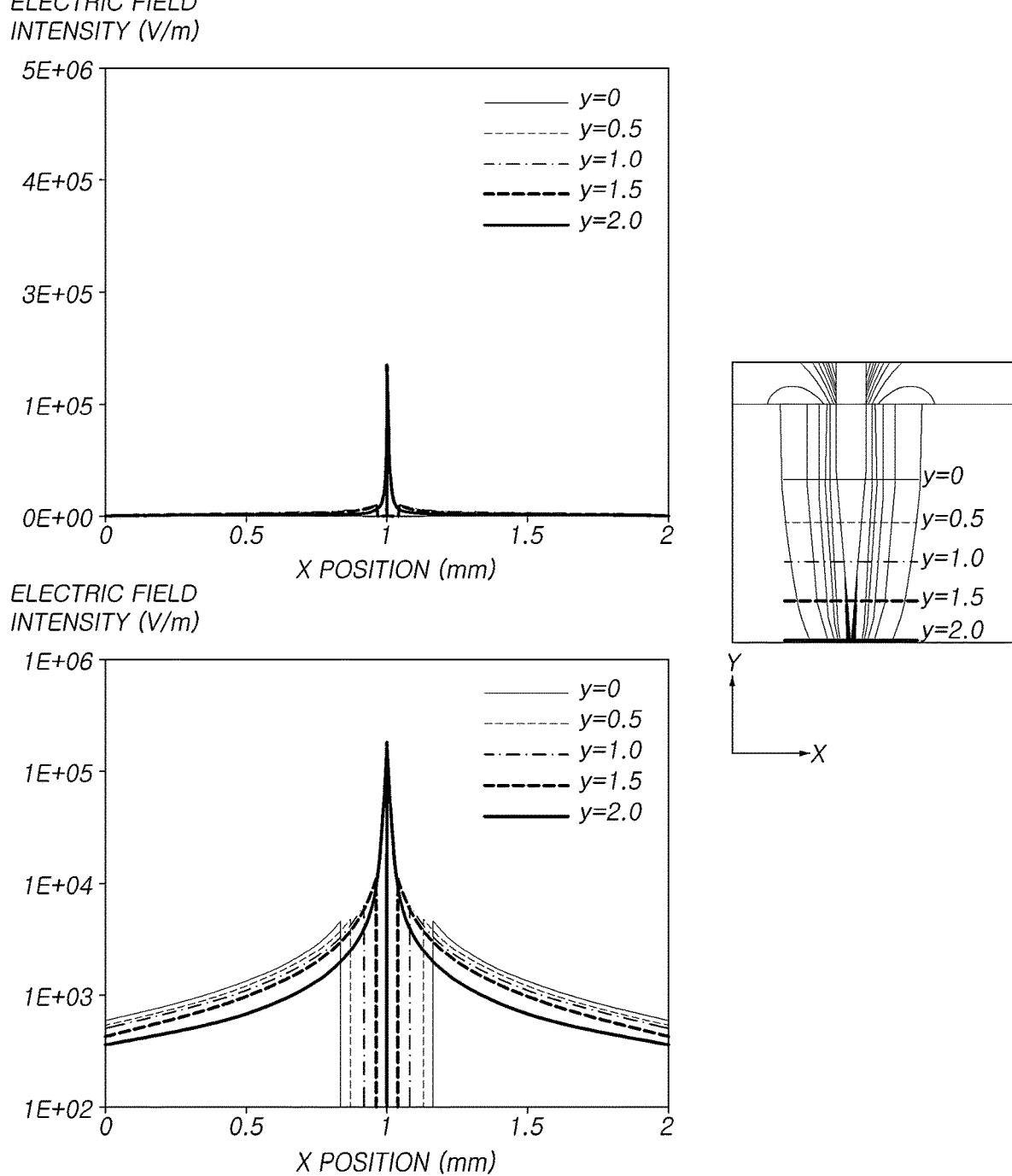
FIG. 7A is a graph showing the electric field intensity in the conventional conical or cylindrical pin.
Figure 7B:
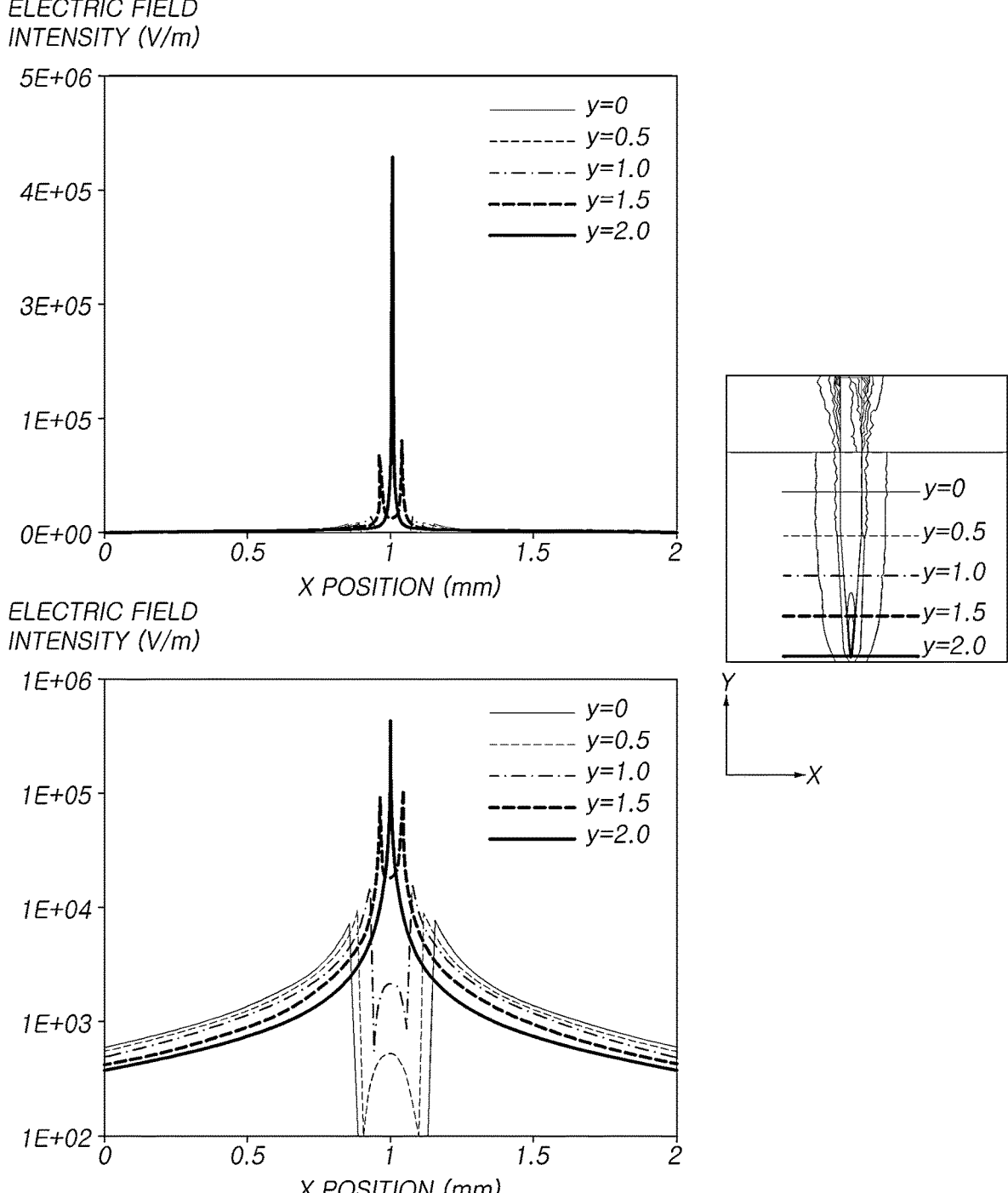
FIG. 7B is a graph showing the electric field intensity in the microblade for electrostimulation according to the embodiment of the present invention.

FIG. 4A shows the distribution of an electric field emitted from the conventional conical or cylindrical pin, and FIG. 4B shows the distribution of an electric field emitted from the microblade for electrostimulation according to the embodiment of the present invention. FIG. 5A is a graph showing the electric field intensity at each position in the longitudinal direction of the conventional conical or cylindrical pin, and FIG. 5B is a graph showing the electric field intensity at each position in the longitudinal direction of the microblade for electrostimulation according to the embodiment of the present invention. FIG. 6A is a schematic cross-sectional diagram showing the electric field generation state in the longitudinal direction of the conventional conical or cylindrical pin, and FIG. 6B is a schematic cross-sectional diagram showing the electric field generation state in the longitudinal direction of the microblade for electrostimulation according to the embodiment of the present invention. FIG. 7A is a graph showing the electric field intensity in the conventional conical or cylindrical pin, and FIG. 7B is a graph showing the electric field intensity in the microblade for electrostimulation according to the embodiment of the present invention.

Referring to FIGS. 4A and 4B, it can be confirmed from simulation data about the electric field distribution that, when power is applied, the electric field is concentrated on the pointed tip of the conical or cylindrical pin 1 and the pointed tip of the tip portion of the microblade 100 of the present invention and is emitted therefrom with high intensity.

Referring to FIGS. 4A, 5A, 6A, and 7A, in the case of the conical or cylindrical pin 1 having a circular cross-section, the electric field that is emitted to the skin is distributed non-uniformly with respect to the longitudinal direction thereof and has low intensity. In contrast, referring to FIGS. 4B, 5B, 6B, and 7B, in the case of the tip portion 10 of the microblade 100 of the present invention, which includes a plurality of planar field emission surfaces, i.e., the pair of first tip inclined surfaces 11a, the pair of second tip inclined surfaces 12a, and the pair of tip connection surfaces 13, the electric field that is emitted to the skin is distributed uniformly with respect to the longitudinal direction thereof and has relatively high intensity.

In particular, referring to FIGS. 5A and 5B, it can be seen that the intensity of the electric field emitted to the skin from the tip portion 10, which includes the pair of first tip inclined surfaces 11a, the pair of second tip inclined surfaces 12a, and the pair of tip connection surfaces 13, is greater than the intensity of the electric field emitted and transmitted to the skin from the conventional conical or cylindrical pin 1.

Referring to FIGS. 6A and 6B, it can be seen that electrical energy, which is an electric field emitted from the pair of first tip inclined surfaces 11a, the pair of second tip inclined surfaces 12a, and the pair of tip connection surfaces 13 of the tip portion, is more strongly emitted and transmitted to the skin in a direction perpendicular to the planar surfaces.

Accordingly, when power is applied to the microblade 100 in the state in which the tip portion is inserted to a predetermined depth in the skin together with the body portion, electrical energy, which is an electric field, is transmitted to the skin with high intensity from the planar field emission surfaces, i.e., the pair of first tip inclined surfaces 11a, the pair of second tip inclined surfaces 12a, and the pair of tip connection surfaces 13, in a direction substantially perpendicular to the planar field emission surfaces. As a result, the efficiency of a skin treatment procedure using electrostimulation may be improved compared to the conventional conical or cylindrical pin.

In addition, compared to the conventional pin 1 having a substantially circular cross-section, the contact area between the tip portion 10, which includes the pair of first tip inclined surfaces 11a, the pair of second tip inclined surfaces 12a, and the pair of tip connection surfaces 13 and thus has a polygonal cross-section, and the skin is increased, whereby electrical energy, which is an electric field generated upon application of power, may be more efficiently emitted and transmitted to the skin.

Referring to FIGS. 1, 2A, 2B, and 3, the body portion 20 is a bar member that extends a predetermined length outwardly from the rear end of the tip portion 10, which is first inserted into the skin. The body portion 20 has a constant outer diameter so as to be inserted into the skin together with the tip portion 10 and is electrically connected to an external power source.

The body portion 20 may include a first body edge portion 21 formed by a pair of first body inclined surfaces 21a, a second body edge portion 22 formed by a pair of second body inclined surfaces 22a, and a pair of body connection surfaces 23, each of which interconnects one of the pair of first body inclined surfaces 21a and one of the pair of second body inclined surfaces 22a adjacent to each other.

In this case, in accordance with the design shape of the body portion 20 that has a constant outer diameter in the longitudinal direction thereof, each of the pair of first body inclined surfaces 21a and the pair of second body inclined surfaces 22a may be formed in a shape of a planar surface that has a constant width and is inclined at a predetermined angle toward the vertices of the first and second body edge portions.

In accordance with the design shape of the body portion 20 that has a constant outer diameter in the longitudinal direction thereof, each of the pair of body connection surfaces 23 may be formed in a shape of a planar surface that has a constant width and is connected to a respective one of the pair of tip connection surfaces 13 of the tip portion via a respective one of the pair of extension surfaces 15.

Although each of the pair of body connection surfaces 23 is illustrated and described as being formed in a shape of a planar surface in order to emit electrical energy, which is an electric field transmitted to the skin when power is applied, in a direction perpendicular thereto, the invention is not limited thereto. Each of the pair of body connection surfaces 23 may be formed in a shape of an arc curved surface.

An angle $\theta$ between the pair of first body inclined surfaces 21a forming the first body edge portion 21 and an angle $\theta$ between the pair of second body inclined surfaces 22a forming the second body edge portion 22 are preferably acute angles smaller than approximately 90°.

An angle $\alpha$ between each of the pair of first body inclined surfaces 21a and an adjacent one of the pair of body connection surfaces 23 and an angle $\alpha$ between each of the pair of second body inclined surfaces 22a and an adjacent one of the pair of body connection surfaces 23 are preferably obtuse angles larger than approximately 90°.

In addition, a vertical distance between the vertex of the first body edge portion 21 at which the pair of first body inclined surfaces 21a meet each other and the vertex of the second body edge portion 22 at which the pair of second body inclined surfaces 22a meet each other is preferably longer than a horizontal distance between the pair of body connection surfaces 23 facing each other.

In this case, the vertical distance and the horizontal distance are maintained constant in accordance with the shape design of the body portion 20 that has a constant outer diameter in the longitudinal direction thereof.

Accordingly, compared to the conventional conical or cylindrical pin having a substantially circular cross-section, the body portion 20, which includes the pair of first body inclined surfaces 21a, the pair of second body inclined surfaces 22a, and the pair of body connection surfaces 23, has a polygonal (e.g., substantially hexagonal) cross-section, similar to the tip portion, and is provided on the outer periphery thereof with a plurality of field emission surfaces that emit electrical energy, which is an electric field emitted to the skin when power is applied, in a direction perpendicular thereto.

Referring to FIGS. 4A, 5A, 6A, and 7A, in the case of the conical or cylindrical pin 1 having a circular cross-section, the electric field that is emitted to the skin is distributed non-uniformly with respect to the longitudinal direction thereof and has low intensity. In contrast, referring to FIGS. 4B, 5B, 6B, and 7B, in the case of the body portion 20 of the microblade 100 of the present invention, which includes a plurality of planar field emission surfaces, i.e., the pair of first body inclined surfaces 21a, the pair of second body inclined surfaces 22a, and the pair of body connection surfaces 23, similar to the tip portion 10, the electric field that is emitted to the skin is distributed uniformly with respect to the longitudinal direction thereof and has relatively high intensity.

In particular, referring to FIGS. 5A and 5B, it can be seen that the intensity of the electric field emitted to the skin from the body portion 20, which includes the pair of first body inclined surfaces 21a, the pair of second body inclined surfaces 22a, and the pair of body connection surfaces 23, is greater than the intensity of the electric field emitted and transmitted to the skin from the conventional conical or cylindrical pin 1.

Referring to FIGS. 6A and 6B, it can be seen that electrical energy, which is an electric field emitted from the pair of first body inclined surfaces 21a, the pair of second body inclined surfaces 22a, and the pair of body connection surfaces 23 of the body portion, is more strongly emitted and transmitted to the skin in a direction perpendicular to the planar surfaces.

Accordingly, when power is applied to the microblade 100 in the state in which the body portion is inserted to a predetermined depth in the skin together with the tip portion, electrical energy, which is an electric field, is transmitted to the skin with high intensity from the planar field emission surfaces, i.e., the pair of first body inclined surfaces 21a, the pair of second body inclined surfaces 22a, and the pair of tip connection surfaces 23, in a direction substantially perpendicular to the planar field emission surfaces. As a result, the efficiency of a skin treatment procedure using electrostimulation may be improved compared to the conventional conical or cylindrical pin.

In other words, the conventional conical or cylindrical pin 1 has a radial electric field formed around the pin, but the microblade 10 according to the embodiment of the present invention forms a non-radial electric field, thereby inducing non-radial heat diffusion. Also, the microblade 10 according to the embodiment of the present invention may induce skin contraction having a directionality when the skin penetrates by forming a non-radial electric field.

In addition, compared to the conventional pin 1 having a substantially circular cross-section, the contact area between the body portion 20, which includes the pair of first body inclined surfaces 21a, the pair of second body inclined surfaces 22a, and the pair of body connection surfaces 23 and thus has a polygonal cross-section, and the skin is increased, whereby electrical energy, which is an electric field generated upon application of power, may be more efficiently emitted and transmitted to the skin.

As is apparent from the above description, the microblade for electrostimulation according to the present invention includes a tip portion and a body portion, each of which includes a first edge portion formed by a pair of first inclined surfaces, a second edge portion formed by a pair of second inclined surfaces, and a pair of connection surfaces, each of which interconnects one of the pair of first inclined surfaces and one of the pair of second inclined surfaces adjacent to each other, and thus has a polygonal cross-section. That is, the microblade for electrostimulation according to the present invention includes a plurality of planar field emission surfaces that emit and transmit an electric field to the skin in a direction perpendicular thereto. Accordingly, compared to the conventional conical or cylindrical pin, an electric field having specific directivity is emitted to the skin with high intensity. As a result, the present invention may increase the efficiency of a skin treatment procedure even when the same amount of power as that applied to the conventional conical or cylindrical pin is applied thereto.

In addition, compared to the conventional conical or cylindrical pin, the microblade of the present invention may obtain the same electric field effect from lower power, and may obtain approximately two-fold higher electric field effect from the same power. In other words, the microblade of the present invention may generate an electric field having relatively high intensity from relatively low power.

In addition, since a plurality of electric fields having different intensities and directivities is emitted to the skin from a plurality of planar field emission surfaces of the tip portion and the body portion, each having a polygonal cross-section, it may be possible to increase skin treatment effect through interaction with another adjacent microblade for electrostimulation.

The effects of the present invention are not limited to the above-mentioned effects, and it should be understood that the effects include all effects that can be inferred from the configuration of the invention described in the detailed description or appended claims of the present invention.

The features as described above are unique features arising from the structure of the microblade according to the embodiment of the present invention and are unique that cannot be implemented by conventional conical or cylindrical pins.

Although specific embodiments of the present invention have been disclosed for illustrative purposes, those skilled in the art will appreciate that various modifications, additions, and substitutions are possible, without departing from the scope and spirit of the invention as disclosed in the accompanying claims.

What is claimed is:

1. A microblade for electrostimulation configured to be inserted to a predetermined depth in a skin to transmit electrical energy to the skin upon receiving power, the microblade comprising:

a tip portion formed to be gradually reduced in outer diameter toward a distal end facing the skin; and a body portion extending outward from a rear end of the tip portion and having a constant outer diameter, wherein the tip portion comprises a first pair of tip inclined surfaces, a second pair of tip inclined surfaces, and a pair of tip connection surfaces, each tip connection surface interconnecting one of the first pair of tip inclined surfaces and one of the second pair of tip inclined surfaces, wherein the body portion comprises a first pair of body inclined surfaces, a second pair of body inclined surfaces, and a pair of body connection surfaces, each body connection surface interconnecting one of the first pair of body inclined surfaces and one of the second pair of body inclined surfaces, wherein, when power is applied to the microblade, an electric field is emitted in a direction perpendicular to planar field emission surfaces formed on outer peripheries of the tip portion and the body portion and is transmitted to the skin, and wherein the pair of tip connection surfaces are disposed between the first pair of tip inclined surfaces and the second pair of tip inclined surfaces and extend to the distal end of the tip portion, while the first pair of tip inclined surfaces and the second pair of tip inclined surfaces terminate before reaching the distal end of the tip portion, such that a width of each of the tip connection surfaces gradually decreases toward the distal end of the tip portion and converges to zero at the distal end of the tip portion.

2. The microblade according to claim 1, wherein each of the pair of tip connection surfaces is formed in a shape of an arc curved surface.

3. The microblade according to claim 1, wherein the tip portion comprises a pair of extension surfaces extending from the pair of body connection surfaces in a boundary area between the tip portion and the body portion so as to be connected to the pair of tip connection surfaces.

4. The microblade according to claim 3, wherein each of the pair of extension surfaces is formed in a shape of a planar surface.

5. The microblade according to claim 1, wherein an angle between the first pair of tip inclined surfaces and an angle between the second pair of tip inclined surfaces are acute angles.

6. The microblade according to claim 1, wherein an angle between each of the first pair of tip inclined surfaces and an adjacent one of the pair of tip connection surfaces and an angle between each of the second pair of tip inclined surfaces and an adjacent one of the pair of tip connection surfaces are obtuse angles.

7. The microblade according to claim 1, wherein a distance between a vertex of a first tip edge portion at which the first pair of tip inclined surfaces meet each other and a vertex of a second tip edge portion at which the second pair of tip inclined surfaces meet each other is longer than a distance between the pair of tip connection surfaces facing each other.

8. The microblade according to claim 1, wherein each of the pair of body connection surfaces is formed in a shape of a planar surface.

9. The microblade according to claim 1, wherein an angle between the first pair of body inclined surfaces and an angle between the second pair of body inclined surfaces are acute angles.

10. The microblade according to claim 1, wherein an angle between each of the first pair of body inclined surfaces and an adjacent one of the pair of body connection surfaces and an angle between each of the second pair of body inclined surfaces and an adjacent one of the pair of body connection surfaces are obtuse angles.

11. The microblade according to claim 1, wherein a distance between a vertex of a first body edge portion at which the first pair of body inclined surfaces meet each other and a vertex of a second body edge portion at which the second pair of body inclined surfaces meet each other is longer than a distance between the pair of body connection surfaces facing each other.

12. The microblade according to claim 1, wherein the tip portion and the body portion have a polyhedral shape with angled surfaces.

13. The microblade according to claim 1, wherein a portion of the tip portion and the body portion have a polygonal shape in a longitudinal section.

* * * * *